US012691233B2

(12) United States Patent
Togo et al.

(10) Patent No.: US 12,691,233 B2
(45) Date of Patent: Jul. 28, 2026

(54) NEBULIZER COMPRISING POWER SUPPLY SYSTEM

(71) Applicant: OMRON HEALTHCARE CO., LTD., Muko (JP)

(72) Inventors: Hidetaka Togo, Kyoto (JP); Hiroko Yoshino, Kyoto (JP); Toshifumi Matsumoto, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 518 days.

(21) Appl. No.: 18/381,679

(22) Filed: Oct. 19, 2023

(65) Prior Publication Data

US 2024/0042143 A1 Feb. 8, 2024

Related U.S. Application Data

(63) Continuation of application No. PCT/JP2022/022772, filed on Jun. 6, 2022.

(30) Foreign Application Priority Data

Jun. 25, 2021 (JP) ................................. 2021-105975

(51) Int. Cl.
A61M 11/00 (2006.01)
A61M 15/00 (2006.01)
(Continued)

(52) U.S. Cl.
CPC ...... A61M 11/005 (2013.01); A61M 15/0085 (2013.01); H02J 50/12 (2016.02); A61M 2205/8243 (2013.01); B05B 17/0623 (2013.01)

(58) Field of Classification Search
CPC ............ A61M 11/005; A61M 15/0085; A61M 2205/8243; B05B 17/0623; H02J 50/12
See application file for complete search history.

(56) References Cited

U.S. PATENT DOCUMENTS 9,962,505 B2 * 5/2018 Schipper ............. B05B 17/0653
2008/0173729 A1 * 7/2008 Weng ................ A61M 15/0085
239/102.2
(Continued)

FOREIGN PATENT DOCUMENTS

JP 2016-007124 A 1/2016
JP 2018-536827 A 12/2018
(Continued)

OTHER PUBLICATIONS

Official Communication issued in International Patent Application No. PCT/JP2022/022772, mailed on Apr. 20, 2023.
(Continued)

*Primary Examiner* — Bradley H Philips
(74) *Attorney, Agent, or Firm* — Keating & Bennett, LLP

(57) ABSTRACT

A nebulizer comprising a power supply system of the present invention performs wireless power supply from a power transmission-side circuit to a power reception-side circuit. The power transmission-side circuit transmits a power to the power reception-side circuit at a certain oscillation frequency through a power transmission coil. In the power reception-side circuit, a power reception coil and a load configure a power reception-side resonance circuit to determine a resonance frequency of the power reception-side resonance circuit. When the resonance frequency of the power reception-side resonance circuit changes due to a change in an impedance of a load during power supply, a control unit controls an oscillation frequency to maintain a power transmission efficiency from the power transmission-side circuit to the power reception-side circuit.

7 Claims, 11 Drawing Sheets

(51) Int. Cl.
    *H02J 50/12*          (2016.01)
    *B05B 17/06*        (2006.01)

(56)              References Cited

U.S. PATENT DOCUMENTS

| | | | |
|---|---|---|---|
| 2015/0349541 | A1 | 12/2015 | Yamamoto et al. |
| 2015/0352713 | A1* | 12/2015 | Takazakura ............. B23B 37/00 |
| | | | 173/2 |
| 2016/0049800 | A1* | 2/2016 | Tanaka ................... H02J 50/12 |
| | | | 307/104 |
| 2018/0313556 | A1 | 11/2018 | Seo |
| 2019/0210055 | A1* | 7/2019 | Maeda ................. B06B 1/0253 |
| 2021/0127754 | A1* | 5/2021 | Tatsuta ................... A24F 40/90 |
| 2022/0305216 | A1* | 9/2022 | Chang ................. A61M 11/005 |

FOREIGN PATENT DOCUMENTS

| | | |
|---|---|---|
| JP | 2019-155346 A | 9/2019 |
| WO | 2014/111972 A1 | 7/2014 |
| WO | 2014/111973 A1 | 7/2014 |
| WO | 2014/178345 A1 | 11/2014 |

OTHER PUBLICATIONS

Official Communication issued in International Patent Application No. PCT/JP2022/022772, mailed on Aug. 2, 2022.
Official Communication issued in corresponding Indian Patent Application No. 202317063709, mailed on Feb. 18, 2026, 10 pages.

* cited by examiner

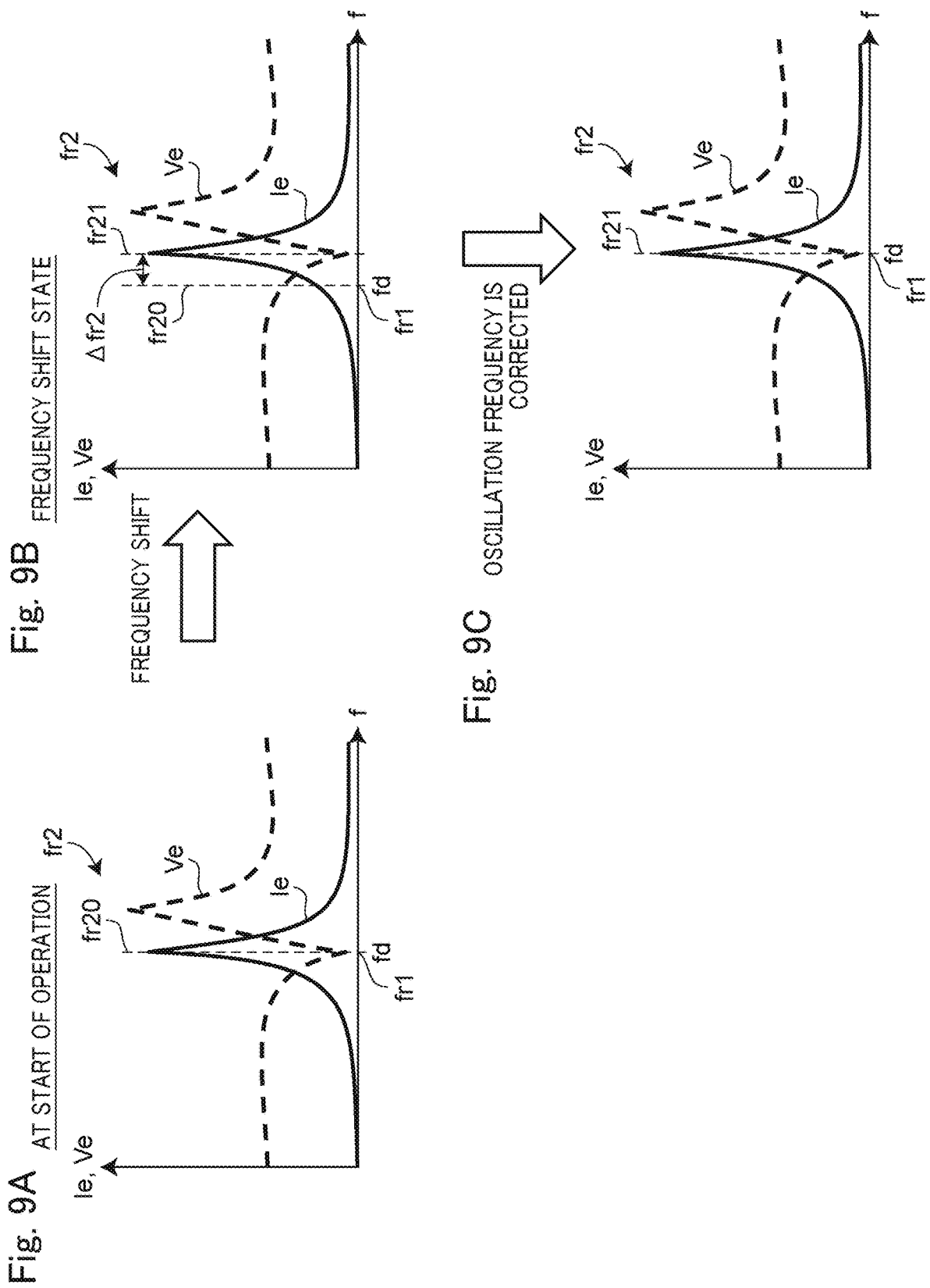
Fig. 9A    AT START OF OPERATION
Fig. 9B    FREQUENCY SHIFT STATE
Fig. 9C    OSCILLATION FREQUENCY IS CORRECTED

Fig. 10A

AT START OF OPERATION

Fig. 10B

FREQUENCY SHIFT STATE

AT START OF OPERATION

LOAD INCREASE STATE

NEBULIZER COMPRISING POWER SUPPLY SYSTEM

CROSS-REFERENCE TO RELATED APPLICATIONS

This is a continuation application of International Application No. PCT/JP2022/022772, with an International filing date of Jun. 6, 2022, which claims priority of Japanese Patent Application No. 2021-105975 filed on Jun. 25, 2021, the entire content of which is hereby incorporated by reference.

TECHNICAL FIELD

The present invention relates to a nebulizer comprising a power supply system, and more particularly to a nebulizer comprising a power supply system that performs wireless power supply from a power transmission-side circuit including a power transmission coil to a power reception-side circuit including a power reception coil, and directly supplies an AC power generated in the power reception coil to a load.

BACKGROUND ART

Conventionally, as this type of power supply system, for example, as disclosed in Patent Document 1 (WO 2014/178345 A), there is known a power supply system in which a power is wirelessly sent from a primary resonance circuit to a secondary resonance circuit, and the power is supplied to a load connected to the secondary resonance circuit, and a power (AC power) generated on the secondary side is not once converted into DC, but is directly supplied to the load.

Patent Document 2 (WO 2014/111972 A) describes that when a power is transmitted from a primary-side power coil to a secondary-side power coil in a non-contact state, a high-frequency voltage generated in the secondary-side power coil is supplied as a drive power to an ultrasonic vibrator as a load.

SUMMARY OF THE INVENTION

According to descriptions of Patent Documents 1, 2, in the power supply system that performs wireless power supply from the power transmission-side circuit including the power transmission coil to the power reception-side circuit including the power reception coil, a circuit configuration is conceivable in which the AC power generated in the power reception coil is not temporarily converted into a DC power but is directly supplied to the ultrasonic vibrator as the load.

However, in the above circuit configuration, there is a possibility that an impedance (a capacitive reactance is dominant, but also it includes an inductive reactance and resistance components) of the ultrasonic vibrator as the load changes during power supply due to influence of temperature fluctuation or the like, and thus a resonance frequency of a resonance circuit configured of the power reception coil and the ultrasonic vibrator changes in the power reception-side circuit. In this case, there arises a problem that a power transmission efficiency from the power transmission-side circuit to the power reception-side circuit decreases.

Therefore, an object of the present invention is to provide a nebulizer comprising a power supply system of a type in which wireless power supply is performed from a power transmission-side circuit to a power reception-side circuit and an AC power generated in a power reception coil is directly supplied to a load, the power supply system capable of preventing a decrease in power transmission efficiency from the power transmission-side circuit to the power reception-side circuit even when an impedance of the load changes.

Solutions to the Problems

In order to achieve the object, a nebulizer of the present disclosure is a nebulizer that atomizes and ejects a liquid, the nebulizer comprising:

a main body lower portion; and a main body upper portion combined with the main body lower portion, the main body lower portion being mounted with a power supply unit, an oscillation unit that receives a power supply from the power supply unit and generates an oscillation output, and a power transmission-side circuit for transmitting the oscillation output to the main body upper portion, the main body upper portion being mounted with a power reception-side circuit for receiving the oscillation output, and an atomization portion including an ultrasonic vibrator configured to atomize a supplied liquid using the oscillation output received, and the nebulizer including a power supply system that performs wireless power supply from the power transmission-side circuit to the power reception-side circuit, wherein the power transmission-side circuit includes a power transmission coil and transmits a power to the power reception-side circuit at a certain oscillation frequency through the power transmission coil, in the power reception-side circuit, a power reception coil and the ultrasonic vibrator as a load including a capacitive reactance configure a power reception-side resonance circuit to determine a resonance frequency of the power reception-side resonance circuit, and the nebulizer includes a control unit that controls the oscillation frequency so as to maintain a power transmission efficiency from the power transmission-side circuit to the power reception-side circuit when a resonance frequency of the power reception-side resonance circuit changes due to a change in an impedance including the capacitive reactance of the ultrasonic vibrator during power supply.

In the present specification, the "load including a capacitive reactance" refers to an ultrasonic vibrator. The ultrasonic vibrator has piezoelectric ceramics and a pair of electrodes provided with the piezoelectric ceramics interposed therebetween, and the piezoelectric ceramics ultrasonically vibrates when a high-frequency voltage is applied between the pair of electrodes.

BRIEF DESCRIPTION OF THE DRAWINGS

FIG. 9A is a diagram showing a relationship between an oscillation frequency fd at a start of operation (power supply) and a current effective value Ie and a voltage effective value Ve in the power transmission-side circuit in a case where the power transmission-side circuit and the power reception-side circuit of the nebulizer are a configuration example of a P-P system.

FIG. 9B is a diagram showing a relationship between the oscillation frequency fd, and the current effective value Ie and the voltage effective value Ve when a frequency shift occurs in FIG. 9A.

FIG. 9C is a diagram showing a relationship between the oscillation frequency fd, and the current effective value Ie and the voltage effective value Ve when the oscillation frequency fd is corrected in FIG. 9B.

FIG. 10A is a diagram showing phases of an oscillation current Io and an oscillation voltage Vo in the case of FIG. 9A.

FIG. 10B is a diagram showing phases of the oscillation current Io and the oscillation voltage Vo in the case of FIG. 9B.

DETAILED DESCRIPTION

Hereinafter, embodiments of the present invention will be described in detail with reference to the drawings.

Schematic Configuration of Nebulizer

Figure 1:
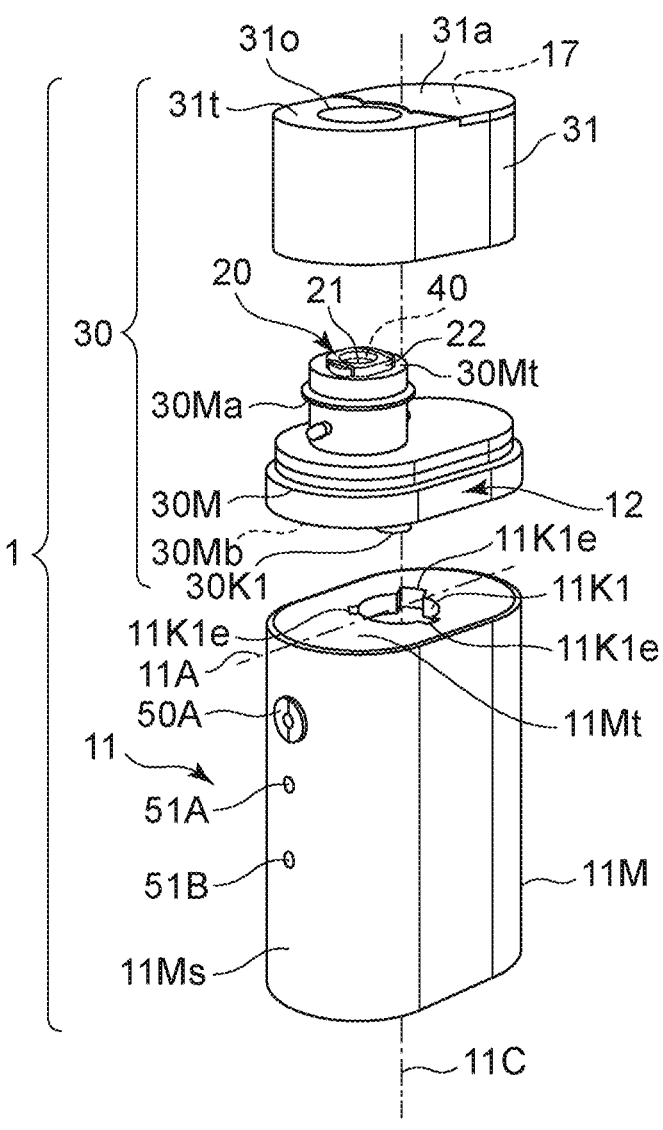
FIG. 1 is a perspective view showing an exploded state of a nebulizer comprising a power supply system of one embodiment of the present invention.

FIG. 1 shows, in an exploded state, a nebulizer (generally indicated by reference sign 1) comprising a power supply system of one embodiment of the present invention. The nebulizer 1 roughly includes a main body 11 as a main body lower portion having a main body casing 11M, and a spray unit 12 as a main body upper portion detachably attached to the main body 11.

In this example, the main body casing 11M forming the main body 11 has an oval planar shape (having a long axis 11A extending from a left front to a right back in FIG. 1), and has a columnar outer shape extending in a direction of a vertical axis 11C (in this example, an up-down direction). A power switch 50A for turning on and off power supply of the nebulizer 1, and display lamps 51A, 51B for indicating an operation state of the nebulizer 1 are provided on a front surface (a left front side surface in FIG. 1) 11Ms of the main body casing 11M. A recess 11K1 having a substantially short cylindrical outer shape is provided in a central portion (through which the vertical axis 11C passes) of an upper wall 11Mt of the main body casing 11M as an element for detachably attaching the main body 11 and the spray unit 12 to each other. In this example, the recess 11K1 has orientation grooves 11K1e, 11K1e, 11K1e extended radially outward in portions corresponding to specific orientations (in this example, three orientations at intervals of 120°) around the vertical axis 11C.

The spray unit 12 includes a base casing 30M having a same oval planar shape as that of the main body casing 11M, and a cover member 31 covering the base casing 30M. The cover member 31 is detachably fitted and attached to the base casing 30M in the direction of the vertical axis 11C (in this example, from above). The base casing 30M and the cover member 31 configure an attachment casing 30.

In this example, the base casing 30M has an upper stage accommodation portion 30Ma protruding upward in a columnar shape at a portion eccentric to a left front side from the vertical axis 11C. The upper stage accommodation portion 30Ma accommodates a horn vibrator 40 as a vibration portion suitable for atomizing a liquid (in this example, a predetermined chemical liquid). In this example, a mesh member 20 is placed on a top surface 30Mt of the upper stage accommodation portion 30Ma in a state of facing the horn vibrator 40. In this example, the mesh member 20 includes a sheet 21 including a mesh portion suitable for atomizing the chemical liquid, and a flange portion 22 that supports a peripheral edge of the sheet 21. The "mesh portion" means an element that has a plurality of fine through holes in the sheet (or a plate material) and allows the liquid to pass through these through holes and be atomized. In this example, the mesh member 20 is adapted to be disposable after one use. In this example, the horn vibrator 40 and the mesh member 20 configure an atomization portion. As a result, a same configuration as that of a commercially available product can be adopted as the atomization portion, and design becomes easy.

A projection 30K1 having a substantially short cylindrical outer shape is provided in a central portion (through which the vertical axis 11C passes) of a bottom wall 30Mb of the spray unit 12 as an element for detachably attaching the main body 11 and the spray unit 12 to each other. In this example, the projection 30K1 has a shape corresponding to the recess 11K1 of the main body casing 11M. That is, the projection 30K1 has a substantially cylindrical shape, and has enlarged diameter portions (not shown) protruding radially outward at portions corresponding to the specific orientations (in this example, the three orientations at intervals of 120°) around the vertical axis 11C. Therefore, when the spray unit 12 (the base casing 30M) is brought close to the main body 11 (the main body casing 11M) in the direction of the vertical axis 11C (in this example, from above), the projection 30K1 is fitted in the recess 11K1, so that the main body 11 and the spray unit 12 are easily attached to each other. Once the spray unit 12 is attached to the main body 11, an attached state is maintained by a frictional force between the recess 11K1 and the projection 30K1. Note that when the user applies a force exceeding the frictional force to separate the spray unit 12 from the main body 11 in the direction of the vertical axis 11C, the spray unit 12 is easily detached from the main body 11.

Figure 6:
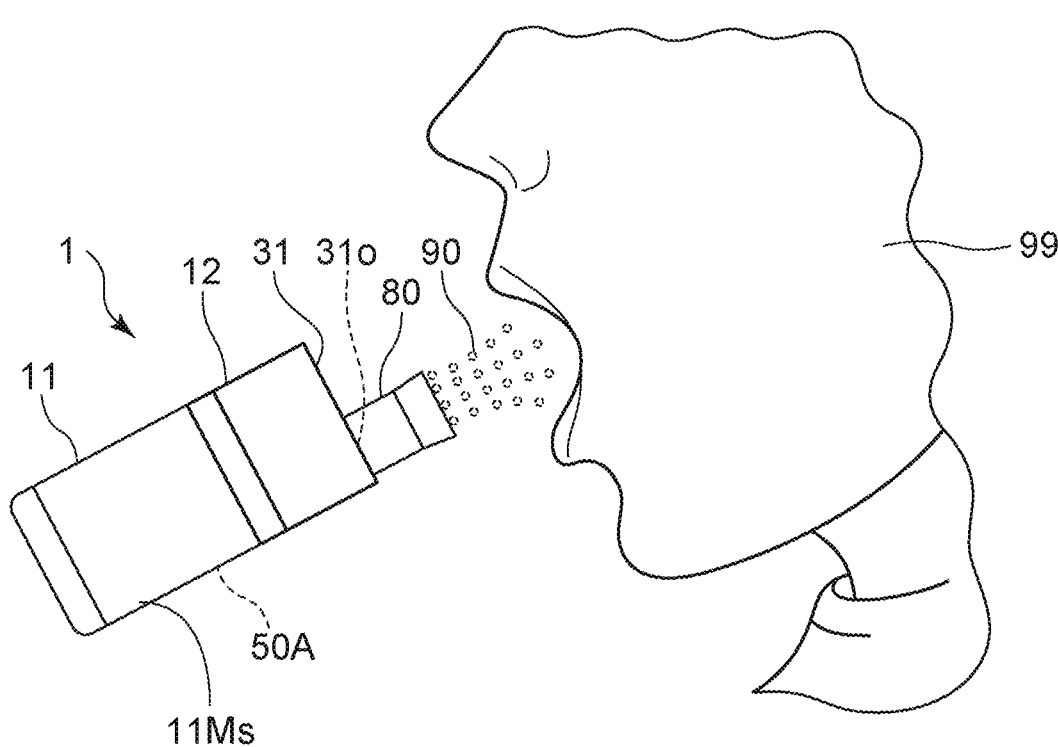
FIG. 6 is a view showing a usage mode of the nebulizer by a user.

The cover member 31 has a same oval planar shape as that of the base casing 30M, and has a cylindrical outer shape extending in the direction of the vertical axis 11C. A circular opening 31o is provided in a portion of a top wall 31t of the cover member 31 eccentric to the left front side from the vertical axis 11C. In a state where the cover member 31 is attached to the base casing 30M, an edge portion of the opening 31o presses the flange portion 22 of the mesh member 20 in the direction of the vertical axis 11C (in this example, from above). As a result, the sheet 21 including the mesh portion is positioned with respect to the horn vibrator 40. In addition, for example, as shown in FIG. 6, a mouthpiece 80 as a pipe member is detachably attached to the opening 31o from an outside of the cover member 31.

In addition, the cover member 31 has a lid portion 31a that can be opened and closed by a hinge in a portion corresponding to a right back side from the opening 31o in the top wall 31t, and a liquid reservoir 17 as a liquid supply portion provided in a position immediately below the lid portion 31a. In a state where the cover member 31 is attached to the base casing 30M, the user can temporarily open the lid portion 31a and put the chemical liquid into the liquid reservoir 17 in this example.

Figure 2:
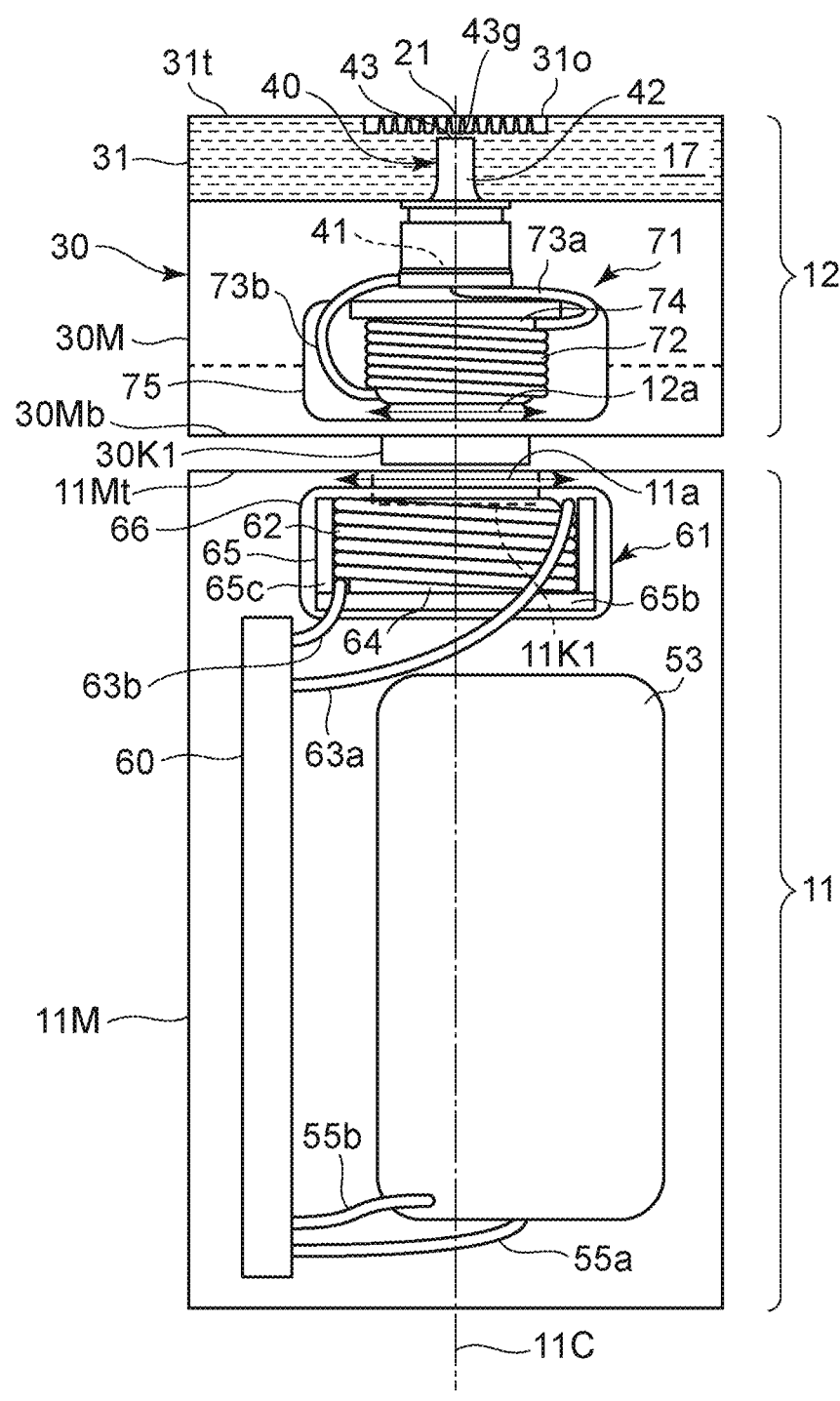
FIG. 2 is a view schematically showing an internal structure of the nebulizer as viewed from a side.
Figure 3:
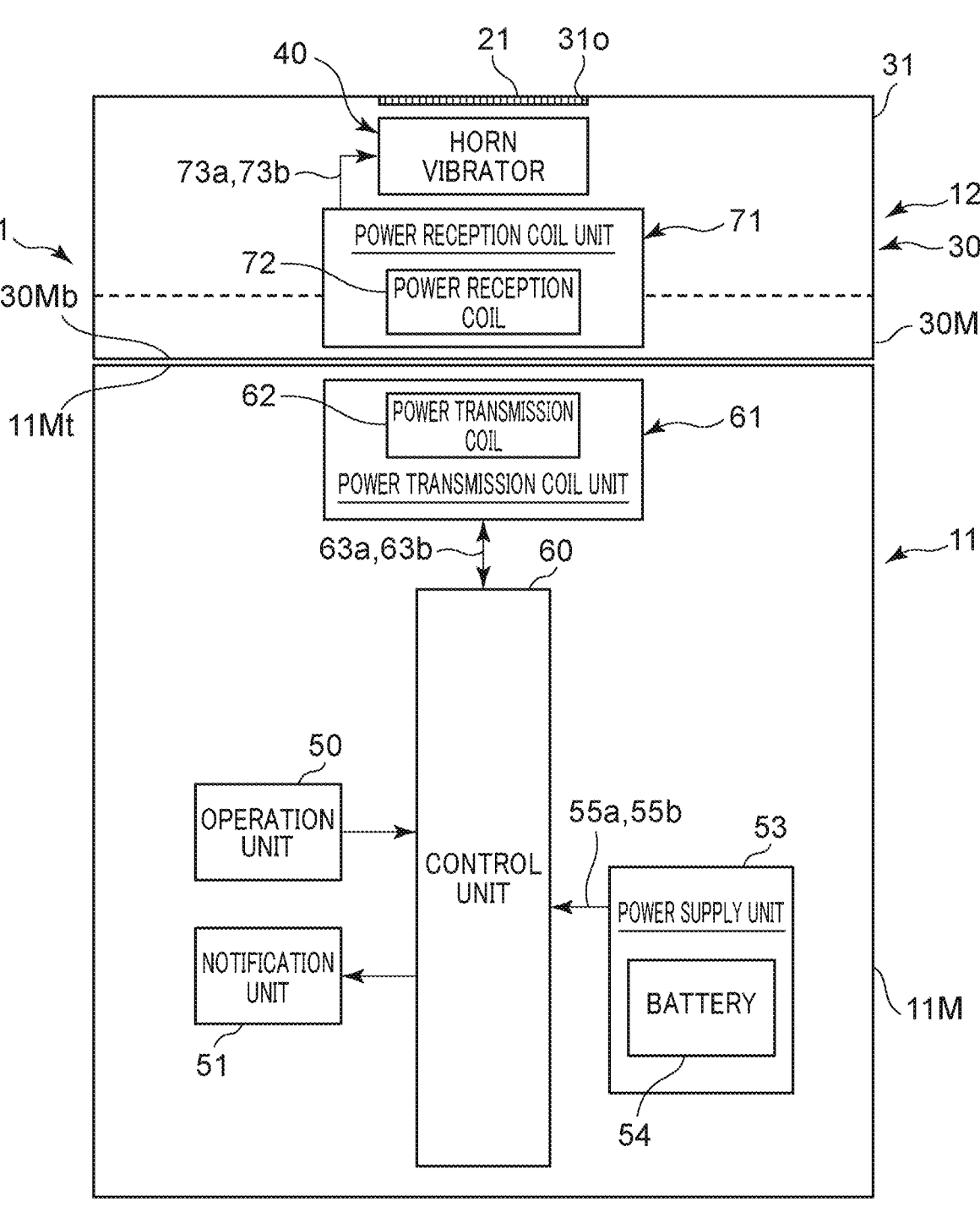
FIG. 3 is diagram showing a block configuration of a control system of the nebulizer.

FIG. 2 schematically shows an internal structure of the nebulizer 1 as viewed from a side. In addition, FIG. 3 shows a block configuration of a control system of the nebulizer 1. Note that, for easy understanding, in FIG. 2, a slight gap for showing the projection 30K1 of the base casing 30M is provided between the base casing 30M of the spray unit 12 and the main body casing 11M. In FIG. 3, the gap between the base casing 30M of the spray unit 12, and the main body casing 11M is not intended.

As can be seen from FIG. 3, the main body 11 mounts and accommodates a control unit 60, an operation unit 50, a notification unit 51, a power supply unit 53, and a power transmission coil unit 61 in the main body casing 11M. In this example, the control unit 60 includes a printed circuit board (PCB) to control overall operation of the nebulizer 1. The operation unit 50 includes the power switch 50A described above, and inputs instructions for turning on and off the power of the nebulizer 1 and various other instructions from the user. The power supply unit 53 includes a battery 54 in this example, and supplies a power to each of the units (including the control unit 60) of the nebulizer 1. The control unit 60 and the power supply unit 53 are connected by wirings 55a, 55b. Note that the power supply unit 53 may be used by converting a commercial power supply. The notification unit 51 includes the display lamps 51A, 51B described above and a buzzer (not shown), and displays an operation state of the nebulizer 1 and/or generates an alarm display or an alarm sound. For example, the display lamp 51A displays on and off of the power, and the display lamp 51B displays a remaining level of the battery 54.

As shown in FIG. 2, the power transmission coil unit 61 includes, in this example, a pole piece 64 made of a substantially cylindrical magnetic body, a yoke 65 made of a magnetic body including an end plate portion 65b in contact with a lower end of the pole piece 64 and an outer peripheral portion 65c that annually surrounds an outer peripheral surface of the pole piece 64 in a separated manner, a power transmission coil 62 that is disposed in a gap between the pole piece 64 and the yoke 65 by winding the pole piece 64, and a sealing case 66 made of a non-magnetic material that integrally covers the pole piece 64, the yoke 65, and the power transmission coil 62. In this example, the power transmission coil unit 61 is disposed on a side facing the spray unit 12 along the upper wall 11Mt of the main body casing 11M. As a result, the power transmission coil 62 is disposed in a specific region along an inner side (a wall surface) of the upper wall 11Mt forming the main body casing 11M, that is, a region 11a (in FIG. 2, an outer diameter of the region 11a is indicated by a double-headed arrow) surrounding the recess 11K1 about the vertical axis 11C. The power transmission coil 62 is connected to the control unit 60 by wirings 63a, 63b. The power transmission coil 62 is used to transmit an oscillation output from the control unit 60 to the spray unit 12 by a wireless power transmission method.

In the spray unit 12, the horn vibrator 40 as the vibration portion, and a power reception coil unit 71 are mounted and housed in the attachment casing 30 (in particular, the base casing 30M).

As shown in FIG. 2, the horn vibrator 40 is configured by integrally combining a vibration surface 43 arranged horizontally so as to face upward, an ultrasonic vibrator 41 arranged at a position separated downward from the vibration surface 43, and a horn 42 arranged between the ultrasonic vibrator 41 and the vibration surface 43 to amplify the vibration of the ultrasonic vibrator 41, and transmit the vibration to the vibration surface 43. In a state where the cover member 31 is attached to the base casing 30M, a gap 43g exists between the sheet 21 including the mesh portion and the vibration surface 43 of the horn vibrator 40. As described later, the chemical liquid in the liquid reservoir 17 is supplied to the gap 43g. The horn vibrator 40 and (the power reception coil 72 of) the power reception coil unit 71 are connected by wirings 73a, 73b.

The power reception coil unit 71 includes a pole piece 74 made of a substantially cylindrical magnetic body, a power reception coil 72 disposed around the pole piece 74 by winding, and a sealing case 75 made of a non-magnetic material integrally covering the pole piece 74 and the power reception coil 72. In this example, the power reception coil unit 71 is disposed on a side facing the main body 11 along an inner side of the bottom wall 30Mb of the base casing 30M. As a result, the power reception coil 72 is disposed in a specific region 12a along an inner side (a wall surface) of the bottom wall 30Mb forming the base casing 30M corresponding to the region 11a of the main body casing 11M where the power transmission coil 62 is disposed (in FIG. 2, an outer diameter of the region 12a is indicated by a double-headed arrow).

As a result, in the state where the main body 11 and the spray unit 12 are attached to each other, the power transmission coil 62 and the power reception coil 72 are disposed in the regions 11a, 12a corresponding to each other with the upper wall 11Mt forming the main body casing 11M and the bottom wall 30Mb forming the attachment casing 30 interposed therebetween. Therefore, during operation, the oscillation output from the control unit 60 can be efficiently transmitted from the main body 11 to the spray unit 12 by the wireless power transmission method via the power transmission coil 62 and the power reception coil 72.

Figure 4:
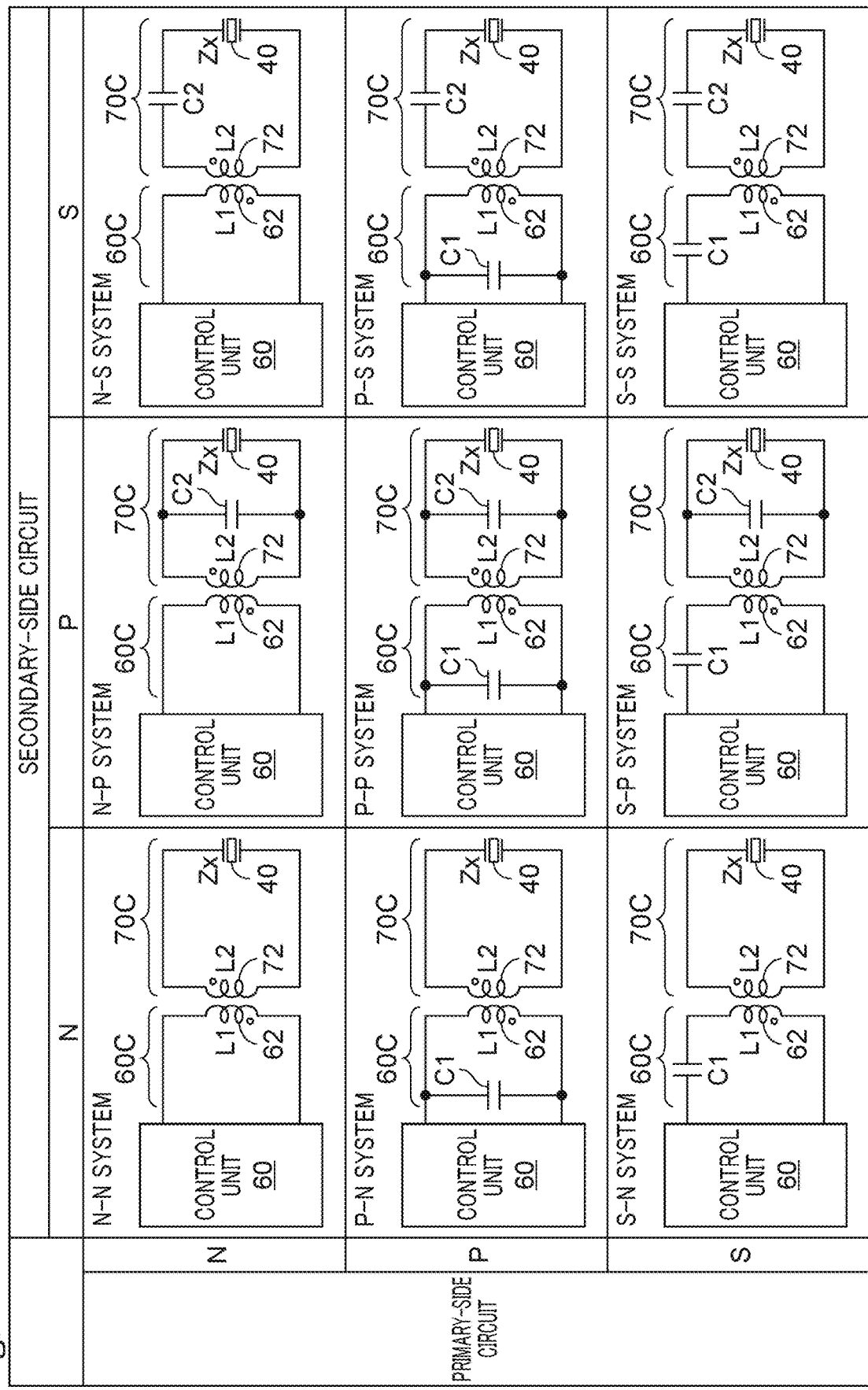
FIG. 4 is a diagram showing various configuration examples that can be taken by a power transmission-side circuit and a power reception-side circuit of the nebulizer.

FIG. 4 shows various configuration examples that can be taken by a power transmission-side circuit 60C and a power reception-side circuit 70C of the nebulizer 1. As shown on a table side (a left column) of FIG. 4, the primary-side circuit (power transmission-side circuit) 60C of the nebulizer 1 may be of three types: an N-type in which a capacitor is not added to the power transmission coil 62 (having an inductive reactance L1); a P-type in which a capacitor (having a capacitive reactance C1) is added in parallel to the power transmission coil 62; and an S-type in which a capacitor (having the capacitive reactance C1) is added in series to the power transmission coil 62. In addition, as shown on a table head (an upper stage) of FIG. 4, the secondary-side circuit (power reception-side circuit) 70C of the nebulizer 1 may be of three types: an N-type in which only the horn vibrator 40 (having an impedance Zx) as a load is added in parallel to the power reception coil 72 (having an inductive reactance L2) and a capacitor is not added; a P-type in which the horn vibrator 40 and a capacitor (having a capacitive reactance C2) are added in parallel to the power reception coil 72; and an S-type in which the horn vibrator 40 and the capacitor (having the capacitive reactance C2) are added in series to the power reception coil 72. By combining the three types of the primary-side circuit (power transmission-side circuit) 60C and the three types of the secondary-side circuit (power reception-side circuit) 70C, as shown in the table of FIG. 4, the power transmission-side circuit 60C and the power reception-side circuit 70C of the nebulizer 1 can have a configuration of a total of nine systems of an N-N system, an N-P system, an N-S system, a P-N system, a P-P system, a P-S system, an S-N system, an S-P system, and an S-S system.

Figures 5A, 5B, 5C:
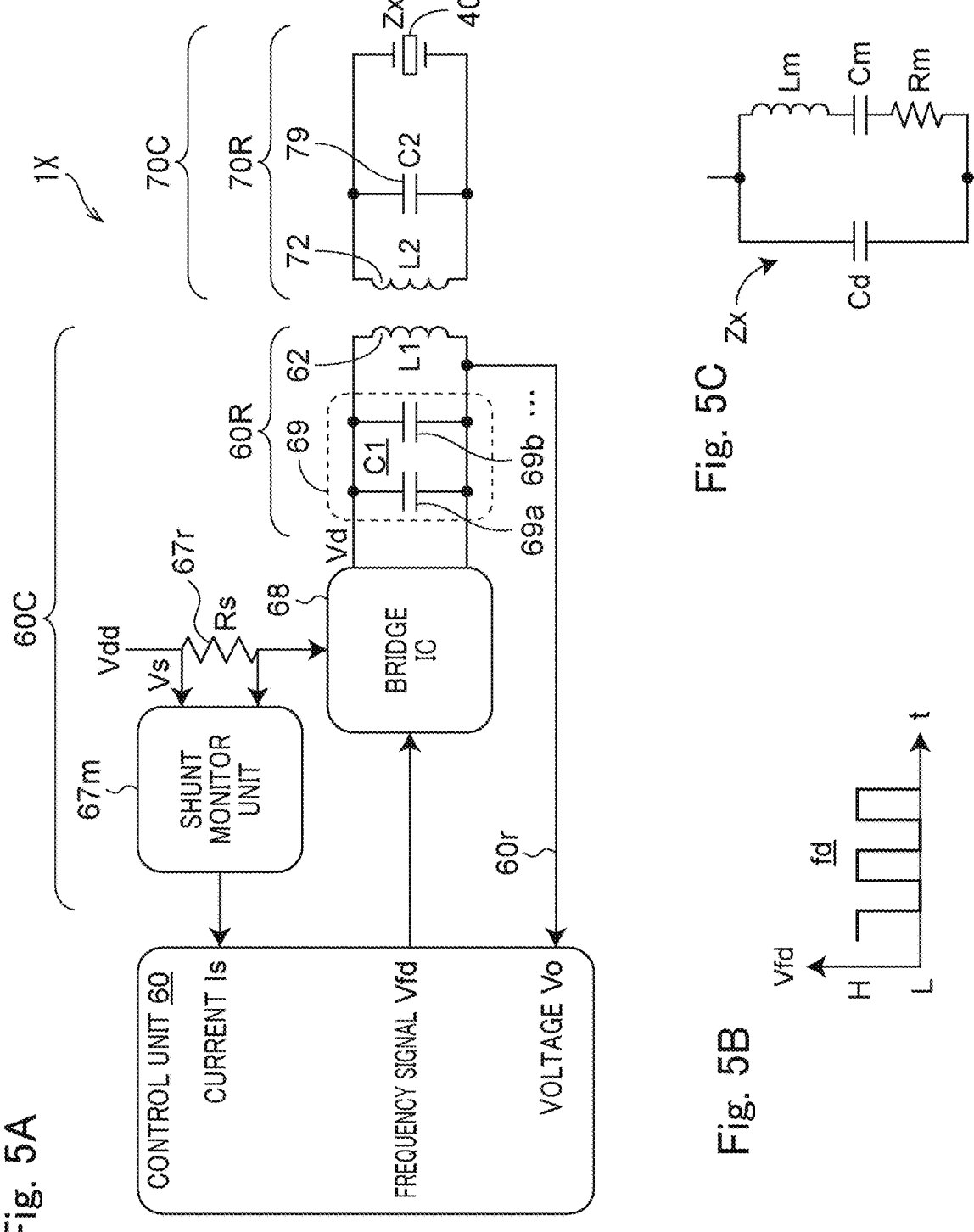
FIG. 5A is a diagram showing a specific configuration when the power transmission-side circuit and the power reception-side circuit of the nebulizer are of a P-P system.
FIG. 5B is a diagram showing a waveform of a signal representing an oscillation frequency generated by a control unit.
FIG. 5C is a diagram showing an equivalent circuit of a horn vibrator as a load.

FIG. 5A shows a specific configuration example in case where the power transmission-side circuit 60C and the power reception-side circuit 70C constituting a power supply system 1X of the nebulizer 1 are of the P-P system.

In this example, the power transmission-side circuit 60C includes the power transmission coil 62 described above, a capacitor 69 (having the capacitive reactance C1) connected in parallel to the power transmission coil 62, a bridge integrated circuit (IC) 68 as an oscillation unit, a shunt resistor 67r connected to the power supply unit 53 (a power supply voltage Vdd), and a shunt monitor unit 67m. Note that, in this example, the elements (including the power transmission coil unit 61) configuring the power transmission-side circuit 60C are mounted on the main body casing 11M configured to be liquid-tight together with the control unit 60. This makes it possible to prevent these elements from being eroded by the chemical liquid.

In this example, the capacitor 69 includes a plurality of capacitors 69a, 69b, . . . that may be connected in parallel to the power transmission coil 62. The plurality of capacitors 69a, 69b, . . . can be adjusted to have a desired capacitive reactance in accordance with a switching signal (not shown) from the control unit 60. As a result, the capacitor 69 can have the capacitive reactance according to the switching signal from the control unit 60. Note that the capacitor 69 may include an element such as, for example, a varicap (a variable capacitor using a depletion layer formed in a semiconductor as a dielectric, in which a capacitive reactance can be changed depending on a magnitude of a reverse voltage), the element being capable of steplessly varying the capacitive reactance by electrical control from the control unit 60.

In this example, the power transmission coil 62 and the capacitor 69 configure a power transmission-side resonance circuit 60R. A resonance frequency fr1 of the power transmission-side resonance circuit 60R is substantially determined by the inductive reactance L1 of the power transmission coil 62 and the capacitive reactance C1 of the capacitor. The bridge IC 68 receives a power supply from the power supply unit 53 (the power supply voltage Vdd) via the shunt resistor 67r, and applies an AC voltage Vd corresponding to a signal Vfd representing an oscillation frequency from the control unit 60 to both ends of the power transmission coil 62 and the capacitor 69 configuring the power transmission-side resonance circuit 60R. Here, as shown in FIG. 5B, the frequency signal Vfd representing the oscillation frequency from the control unit 60 is a digital signal having a rectangular waveform that alternately repeats a high (H) level and a low (L) level at an oscillation frequency fd. The bridge IC 68 generates the AC voltage Vd alternating at the oscillation frequency fd, and applies the AC voltage Vd to the both ends of the power transmission coil 62 and the capacitor 69 configuring the power transmission-side resonance circuit 60R as a power for the power transmission. The power transmission coil 62 and the capacitor 69 resonate at a resonance frequency fr1 (=fd) in this example in accordance with the power supply from the bridge IC 68, and thus generate an oscillation output PO, and send the oscillation output PO toward the power reception-side circuit 70C.

Figures 10A, 10B:
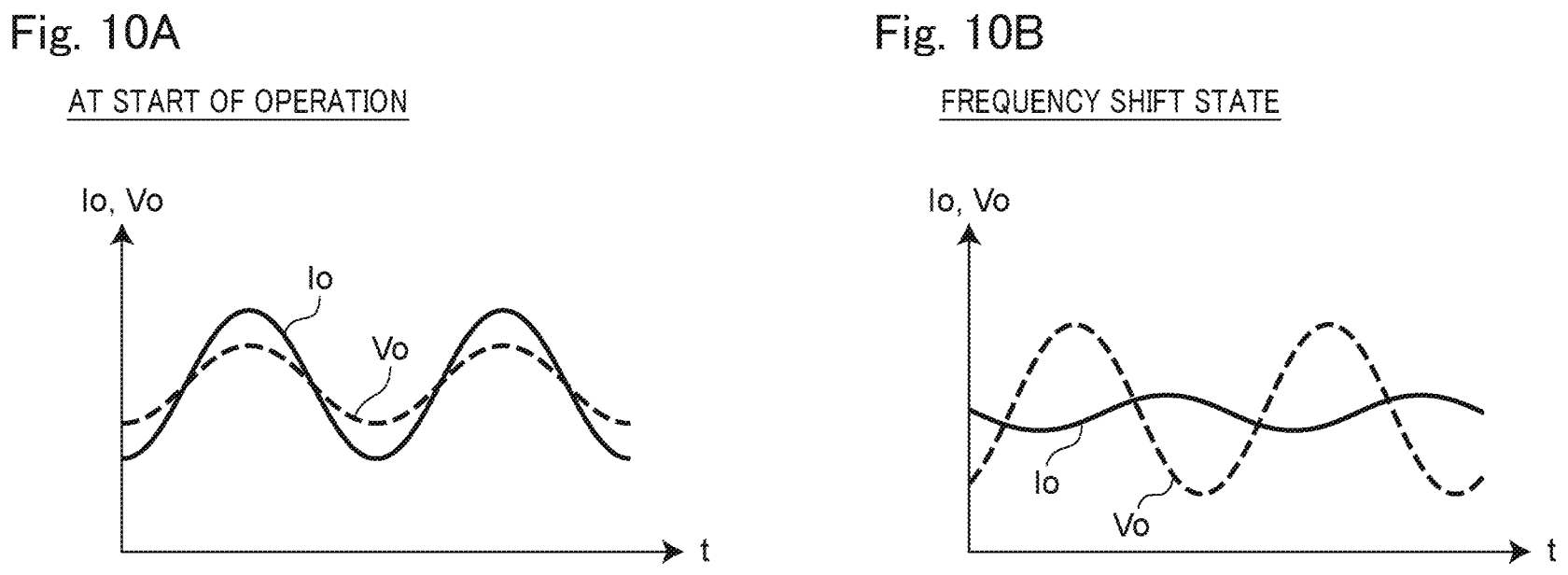

During the power transmission, a current Is for driving the power transmission-side resonance circuit 60R flows from the power supply unit 53 (the power supply voltage Vdd) to the bridge IC 68 through the shunt resistor 67r (having a resistance value Rs) with lapse of a time t, for example, as illustrated in FIG. 10A. As a result, a voltage Vs drops to the shunt resistor 67r. The shunt monitor unit 67m shown in FIG. 5A observes the voltage Vs and inputs a signal representing the current Is (=Vs/Rs) to the control unit 60. Further, to the control unit 60 is input a signal representing an oscillation voltage Vo in the power transmission-side resonance circuit 60R via a signal line 60r connected to one end of the power transmission-side resonance circuit 60R. In this example, the shunt resistor 67r, the shunt monitor unit 67m, and the signal line 60r configure a detection unit that detects a voltage value and/or a current value for the power transmission in the power transmission-side circuit 60C. The control unit 60 can calculate an effective value (referred to as a "current effective value Ie") of the current Is and an effective value (referred to as a "voltage effective value Ve") of the oscillation voltage Vo. Further, the control unit 60 can calculate a product of the current effective value Ie and the voltage effective value Ve as the oscillation power (or an amount substantially corresponding to the oscillation power) PO in the power transmission-side circuit 60C.

In the example of FIG. 5A, the power reception-side circuit 70C includes the power reception coil 72 described above, a capacitor 79 (having a capacitive reactance C2) connected in parallel to the power reception coil 72, and the horn vibrator 40 (in particular, the ultrasonic vibrator 41) described above that is connected in parallel to the power reception coil 72 and the capacitor 79.

Although the ultrasonic vibrator 41 of the horn vibrator 40 is not shown because it is known, the ultrasonic vibrator includes piezoelectric ceramics and a pair of electrodes provided with the piezoelectric ceramics interposed therebetween, and the piezoelectric ceramics ultrasonically vibrates when a high-frequency voltage is applied between the pair of electrodes. As illustrated in FIG. 5C, an equivalent circuit of the ultrasonic vibrator 41 is represented by a capacitive reactance Cd between the pair of electrodes, and an inductive reactance Lm, a capacitive reactance Cm, and a resistance component Rm connected in series, which are connected in parallel to the capacitive reactance Cd. In this example, these elements Cd, Lm, Cm, and Rm are collectively referred to as an impedance Zx.

In this example, the power reception coil 72, the capacitor 79, and the horn vibrator 40 configure a power reception-side resonance circuit 70R. A resonance frequency fr2 of the power reception-side resonance circuit 70R is determined by the inductive reactance L2 of the power reception coil 72, the capacitive reactance C2 of the capacitor 79, and the impedance Zx of the horn vibrator 40. At a start of operation, the resonance frequency fr2 of the power reception-side resonance circuit 70R is 180 kHz.

As described at the beginning of the present specification, in the circuit configuration described above, the impedance Zx of the horn vibrator 40 (in particular, the ultrasonic vibrator 41) as the load may change during the power supply due to influence of a temperature fluctuation and the like, and thus the resonance frequency fr2 of the power reception-side resonance circuit 70R can change. Hereinafter, operation of the control unit 60 for coping with this will be described.

Operation of Nebulizer

A user who intends to use the nebulizer 1 attaches the spray unit 12 to the main body 11, and puts the chemical liquid adapted to the spray unit 12 into the liquid reservoir 17 of the attached spray unit 12. As a result, the chemical liquid put in the liquid reservoir 17 is supplied to the gap 43g (see FIG. 2) between the sheet 21 and the vibration surface 43 of the horn vibrator 40. In addition, the mouthpiece 80 is attached to the opening 31o of the spray unit 12. Subsequently, as shown in FIG. 6, a user 99 tilts the entire nebulizer 1 toward a front side, brings the mouthpiece 80 close to a mouth, and holds the mouthpiece in the mouth. In this state, the user 99 turns on the power switch 50A provided on front surface 11Ms of the main body 11.

Figure 7:
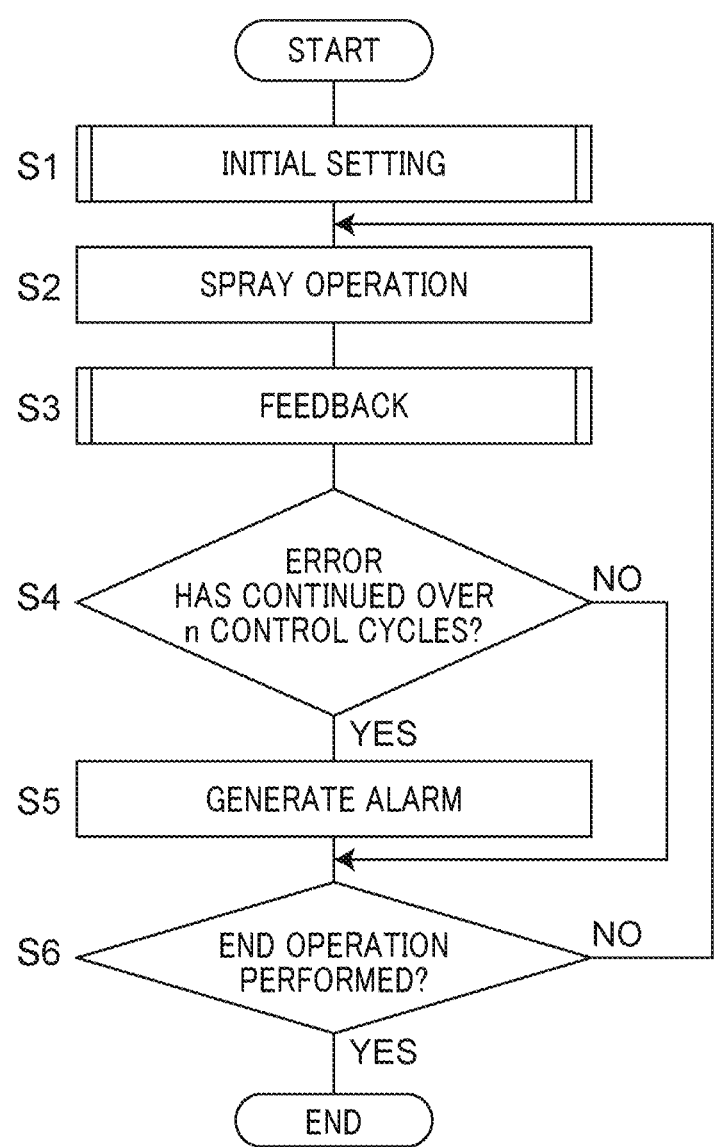
FIG. 7 is a diagram showing a schematic operation flow by the control unit of the nebulizer.

Then, the control unit 60 executes the control shown in an operation flow (main flow) of FIG. 7.

First, as shown in step S1 of FIG. 7, the control unit 60 performs initial setting.

In this example, as described above, it is assumed that the resonance frequency fr2 (an initial value is defined as fr20) of the power reception-side resonance circuit 70R in the spray unit 12 is 180 kHz at the start of operation. Then, for example, as shown in FIG. 9A (a horizontal axis represents a frequency f, and a vertical axis represents the current effective value Ie, and the voltage effective value Ve), when the oscillation frequency fd (that is, the resonance frequency fr1 of the power transmission-side resonance circuit 60R) matches the resonance frequency fr2 (the initial value fr20) of the power reception-side resonance circuit 70R, the current effective value Ie for driving the power transmission-side resonance circuit 60R shows a peak. The voltage effective value Ve shows a steep change when the oscillation frequency fd is swept across the resonance frequency fr2 (=fr20). Therefore, the control unit 60 can find the resonance frequency fr2 (the initial value fr20) of the power reception-side resonance circuit 70R by, for example, calculating a ratio (voltage/current ratio) between the voltage effective value Ve and the current effective value Ie for each oscillation frequency fd as a voltage-to-current relationship.

Accordingly, the control unit 60 adjusts the capacitive reactance of the capacitor 69 by the switching signal to match the resonance frequency fr1 of the power transmission-side resonance circuit 60R with fr20 in this example. As a result, the power transmission-side resonance circuit 60R and the power reception-side resonance circuit 70R are brought into a tuned state. Then, the processing returns to the main flow of FIG. 7.

Next, in step S2 of FIG. 7, the control unit 60 starts spray operation. Specifically, the control unit 60 generates the oscillation output PO having the oscillation frequency fd set as a target frequency (fr 20 in this example). The oscillation output PO is transmitted from the power transmission coil 62 to the power reception coil 72 for the atomization portion (in this example, the atomization portion is configured of the horn vibrator 40 and the mesh member 20) by wireless power transmission using magnetic coupling. As a result, the oscillation output PO is applied to the horn vibrator 40, and the chemical liquid is atomized by the atomization portion. As shown in FIG. 6, the atomized chemical liquid becomes an aerosol 90, and is inhaled by the user 99 through the mouthpiece 80 in this example.

Figures 8A, 8B:
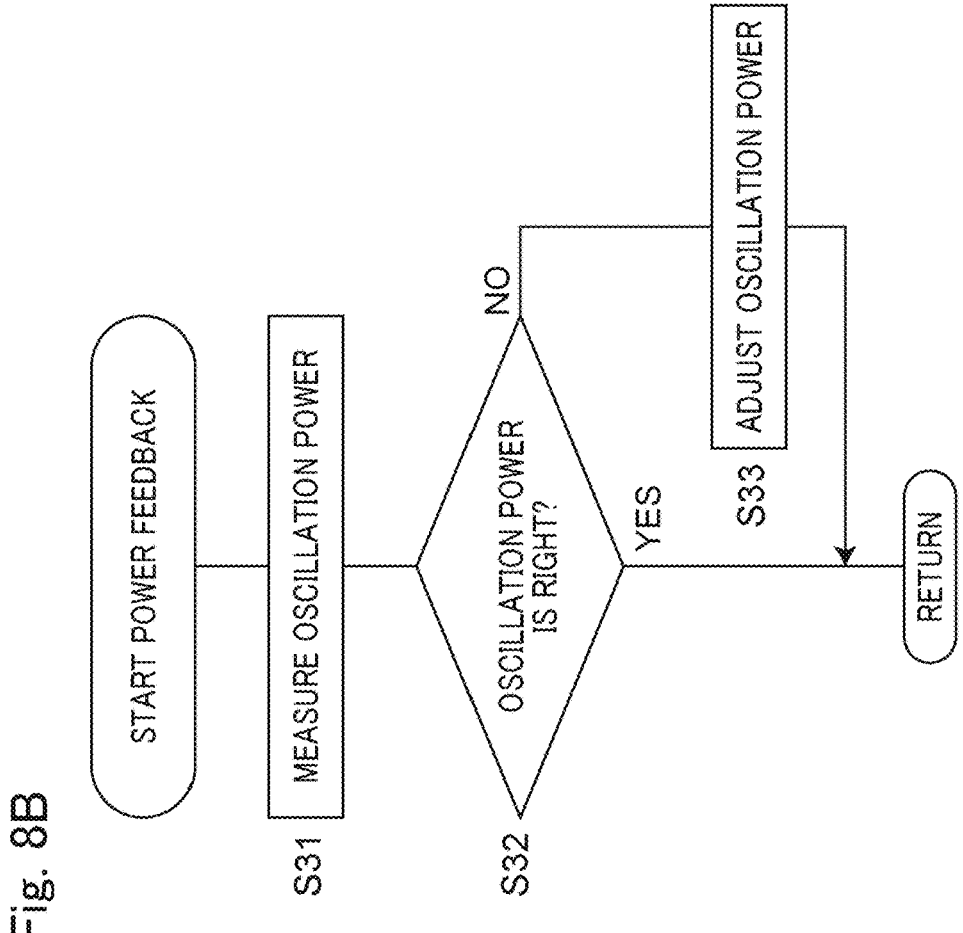
FIG. 8A is a diagram showing a specific operation flow of feedback included in the operation flow of FIG. 7.
FIG. 8B is a diagram showing another specific operation flow of feedback included in the operation flow of FIG. 7.

During the spray operation (during the power supply), as shown in step S3 of FIG. 7, the control unit 60 performs feedback processing. Specifically, as shown in step S21 of FIG. 8A, the control unit 60 determines whether or not the resonance frequency fr2 of the power reception-side resonance circuit 70R shifts from currently set oscillation frequency fd on the basis of the voltage-to-current relationship (in this example, the voltage/current ratio) in the power transmission-side circuit 60C (described above using FIG. 9A).

Here, when the resonance frequency fr2 of the power reception-side resonance circuit 70R matches the currently set oscillation frequency fd (NO in step S21 of FIG. 8A), the processing returns to the main flow of FIG. 7 as it is. On the other hand, when the resonance frequency fr2 of the power reception-side resonance circuit 70R shifts even slightly from the currently set oscillation frequency fd (YES in step S21 in FIG. 8A), the control unit 60 corrects the oscillation frequency fd as shown in step S22.

Specifically, for example, as shown in FIG. 9B, it is assumed that the resonance frequency fr2 of the power reception-side resonance circuit 70R is shifted by Δfr2 from the initial value fr20 to an other value (in this example, fr21). At this time, as shown in FIG. 9C, the control unit 60 matches the oscillation frequency fd with the other value fr21 on the basis of the voltage-to-current relationship (in this example, the voltage/current ratio) in the power transmission-side circuit 60C. More specifically, for example, the control unit 60 shifts the oscillation frequency fd in a direction in which the voltage/current ratio becomes small by the current effective value Ie becoming large and/or the voltage effective value Ve becoming small. Note that, as shown in FIGS. 10A to 10B, the shift of the resonance frequency fr2 of the power reception-side resonance circuit 70R may cause a shift of a phase angle between an oscillation current Io (=Is) and the oscillation voltage Vo in the power transmission-side resonance circuit 60R. Therefore, the control unit 60 may shift the oscillation frequency fd in a direction in which the phase difference (phase angle) between the oscillation current Io and the oscillation voltage Vo becomes small. With this, the control unit 60 adjusts the capacitive reactance of the capacitor 69 by the switching signal to match the resonance frequency fr1 of the power transmission-side resonance circuit 60R with fr21 in this example. As a result, the power transmission-side resonance circuit 60R and the power reception-side resonance circuit 70R are brought into the tuned state. This can prevent a decrease in power transmission efficiency from the power transmission-side circuit 60C to the power reception-side circuit 70C. Then, the processing returns to the main flow of FIG. 7.

In addition, in step S3 of FIG. 7, the control unit 60 performs power feedback processing. Specifically, as shown in step S31 of FIG. 8B, the control unit 60 measures a present oscillation power PO in the power transmission-side circuit 60C. That is, the control unit 60 calculates the product of the current effective value Ie and the voltage effective value Ve as the present oscillation power PO in the power transmission-side circuit 60C. Subsequently, as described in step S32, the control unit 60 determines whether or not the oscillation power PO deviates from a predetermined target power value (for example, a value defined as a product specification of the nebulizer) POtarget. For example, when the present oscillation power PO falls within a range of ±5% from the target power value POtarget, it is determined that present oscillation power PO in the power transmission-side circuit 60C falls within an allowable range (YES in step S32 in FIG. 8B). Then, the processing returns to the main flow of FIG. 7 as it is. On the other hand, when the present oscillation power PO deviates from the target power value POtarget by more than ±5% (NO in step S32 in FIG. 8B), it is determined that the present oscillation power PO in the power transmission-side circuit 60C is outside the allowable range (error). Then, as shown in step S33, the control unit 60 adjusts an amplitude of the AC voltage Vd applied to the power transmission-side resonance circuit 60R (the both ends of the power transmission coil 62 and the capacitor 69) by the bridge IC 68 such that the present oscillation power PO falls within the allowable range. As a result, the oscillation power PO in the power transmission-side circuit 60C can be maintained within the allowable range from the target power value POtarget. Then, the processing returns to the main flow of FIG. 7.

Next, in step S4 of FIG. 7, the control unit 60 determines whether or not an error has continued over n control cycles.

Here, in this example, it is assumed that one control cycle (cycle of repeating steps S2 to S6 in FIG. 7) of the control unit 60 is 10 milliseconds, and n=3, and therefore, a period corresponding to the n control cycle is 30 milliseconds. In addition, the "error" means that the voltage effective value Ve in the power transmission-side circuit 60C exceeds a predetermined specified value, the current effective value Ie in the power transmission-side circuit 60C falls below a predetermined specified value, and/or the oscillation power PO deviates from the target power value POtarget beyond the allowable range.

Here, when the error does not continue (NO in step S4 in FIG. 7), the control unit 60 returns to step S2 and continues the spray operation unless the user performs an end operation (turning off the power switch 50A) (NO in step S6). On the other hand, when the error continues over the n control cycles (YES in step S4 in FIG. 7), the processing proceeds to step S5, in which the control unit 60 causes the notification unit 51 to output an alarm signal indicating occurrence of the error and notify the user of the occurrence of the error. For example, the notification unit 51 displays the alarm by blinking the display lamp 51A or 51B described above and/or generates an alarm sound by a buzzer (not shown).

As a result, the user can know the occurrence of the error. Therefore, for example, the user can take measures such as stopping (turning off) and restarting the spray operation of the nebulizer 1, and when errors frequently occur, the user can request a service department of the manufacturer to repair the nebulizer 1.

Thereafter, when the user performs the end operation (YES in step S6), the spray operation ends.

As described above, according to the nebulizer 1, even when the impedance Zx of the horn vibrator 40 (in particular, the ultrasonic vibrator 41) changes during the power supply (during the spray operation), the power transmission efficiency from the power transmission-side circuit 60C to the power reception-side circuit 70 C can be prevented from decreasing. As a result, the atomization portion including the horn vibrator 40 can stably atomize and eject the supplied liquid using the received oscillation output PO.

Modified Example

Figures 11A, 11B, 11C:
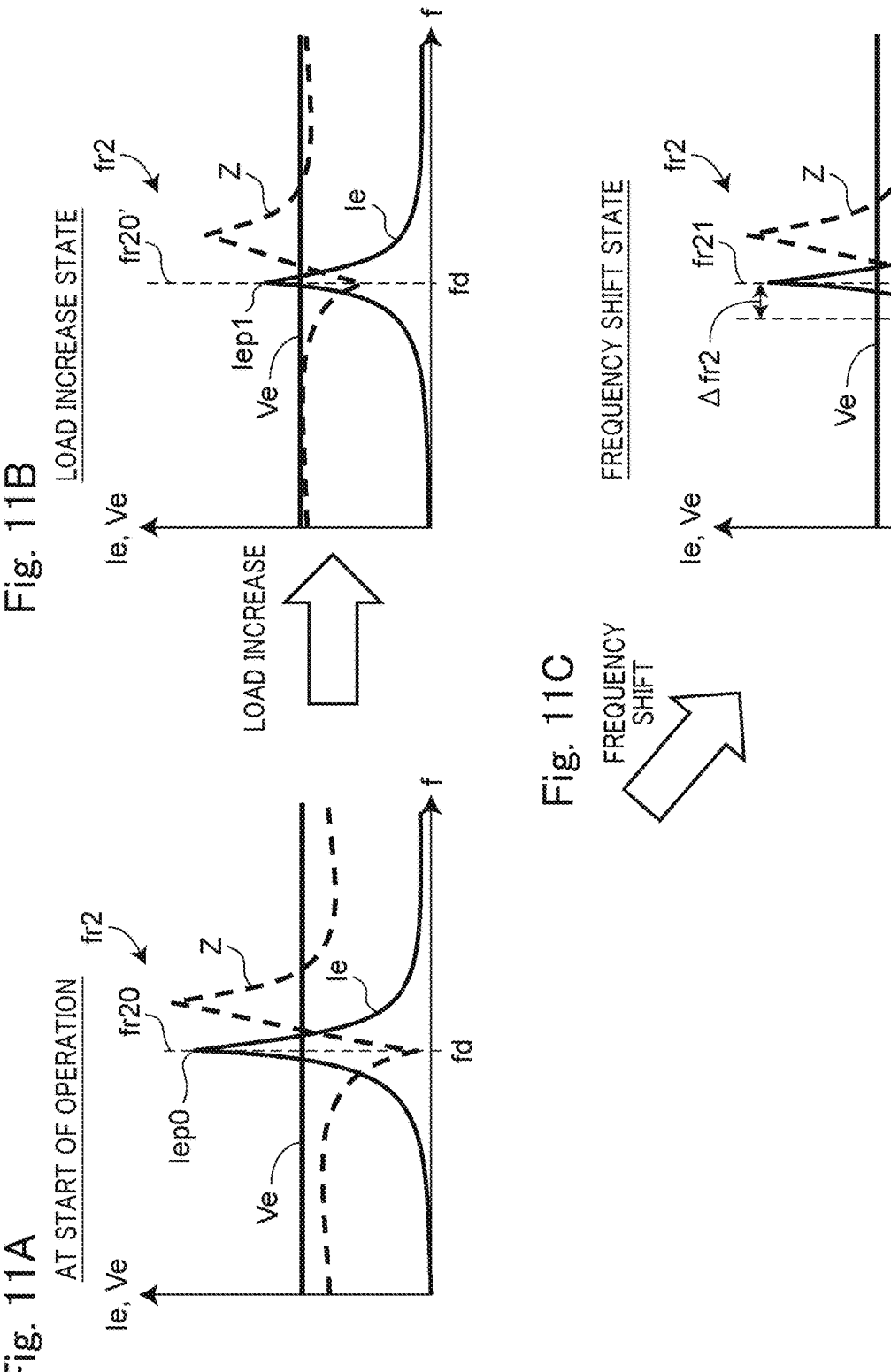
FIG. 11A is a diagram showing a relationship between the oscillation frequency fd at a start of operation (power supply), and the current effective value Ie and the voltage effective value Ve in the power transmission-side circuit in a case where the power transmission-side circuit and the power reception-side circuit of the nebulizer are a configuration example of an N-P system or an N-S system.
FIG. 11B is a diagram showing a relationship between the oscillation frequency fd, and the current effective value Ie and the voltage effective value Ve when a load increase occurs in FIG. 11A.
FIG. 11C is a diagram showing a relationship between the oscillation frequency fd, and the current effective value Ie and the voltage effective value Ve when a frequency shift occurs in FIG. 11A.

In the above example, while the case where the power transmission-side circuit 60C and the power reception-side circuit 70C of the nebulizer 1 are of the P-P system has been described, the present invention is not limited thereto. As shown in FIG. 4, various configuration examples that can be taken by the power transmission-side circuit 60C and the power reception-side circuit 70C of the nebulizer 1. For example, when the power transmission-side circuit 60C and the power reception-side circuit 70C of the nebulizer 1 are of the N-S system or the N-P system, the relationship between the oscillation frequency fd at a start of operation (power supply), and the current effective value Ie and the voltage effective value Ve in the power transmission-side circuit 60C is obtained as shown in FIG. 11A. This relationship is considered to be basically similar to the relationship shown in FIG. 9A. That is, in the N-S system or the N-P system, since the power transmission-side resonance circuit 60R is not provided in the power transmission-side circuit 60C, the oscillation frequency fd is swept under a condition that the voltage effective value Ve is constant. At this time, in FIG. 11A, similarly to FIG. 9A, when the oscillation frequency fd matches the resonance frequency fr2 (initial value fr20) of the power reception-side resonance circuit 70R, the current effective value Ie for driving the power transmission-side resonance circuit 60R shows a peak. Note that a ratio (voltage/current ratio) Z between the voltage effective value Ve and the current effective value Ie shows a steep change when the oscillation frequency fd is swept across the resonance frequency fr2 (=fr20). Therefore, the control unit 60 can similarly execute the operation flow in FIG. 7 (the processing includes the frequency feedback processing in FIG. 8A and the power feedback processing in FIG. 8B).

Therefore, the control unit 60 can find the resonance frequency fr2 (the initial value fr20) of the power reception-side resonance circuit 70R by, for example, calculating the ratio Z between the voltage effective value Ve and the current effective value Ie for each oscillation frequency fd as the voltage-to-current relationship in FIG. 11A (step S1 in FIG. 7).

In addition, it is assumed that an impedance Zx of the horn vibrator 40 (in particular, the ultrasonic vibrator 41) as the load changes during the spray operation (during the power supply), and thus the resonance frequency fr2 of the power reception-side resonance circuit 70R is shifted by Δfr2 from the initial value fr20 to an other value (in this example, fr21), for example, as shown in FIG. 11C. At this time, the control unit 60 matches the oscillation frequency fd with the other value fr21 on the basis of the voltage-to-current relationship Z (in this example, the voltage/current ratio) in the power transmission-side circuit 60C (step S22 in FIG. 8A), as shown in FIG. 9C.

In addition, it is assumed that the impedance Zx of the horn vibrator 40 (in particular, the ultrasonic vibrator 41) as the load increases during the spray operation (during the power supply), and thus a peak of the current effective value Ie in the power transmission-side circuit 60C changes from an initial value Iep0 to an other smaller value Iep1, for example, as shown in FIG. 11B. At this time, the control unit 60 can calculate the product of the current effective value Ie and the voltage effective value Ve as a present oscillation power PO in the power transmission-side circuit 60C, and determine whether the oscillation power PO deviates from a predetermined target power value POtarget (steps S31 to S32 in FIG. 8 B).

Note that when the impedance Zx of the horn vibrator 40 (in particular, the ultrasonic vibrator 41) as the load increases, the resonance frequency fr2 of the power reception-side resonance circuit 70R may be shifted (in the example of FIG. 11B, the initial value fr2 is shifted to fr20'.). This shift can be handled by the processing of step S22 of FIG. 8A described above.

Note that in the example of FIG. 4 described above, the power transmission-side circuit 60C and the power reception-side circuit 70C of the nebulizer 1 can have a total of nine configurations of the N-N, N-P, N-S, P-N, P-P, P-S, S-N, S-P, and S-S systems. However, the present invention is not limited thereto. For example, in the table (body) of FIG. 4, a configuration in which features of the N-P system shown in a center of an upper stage and the N-S system shown in the right of the upper stage are combined is also possible. For example, a configuration may be employed in which a first capacitor may be added in parallel to the power reception coil 72, and a second capacitor and the horn vibrator 40 are added in series to the parallel connection between the power reception coil 72 and the first capacitor. Alternatively, a configuration may be employed in which a first capacitor may be added in series to the power reception coil 72, and a second capacitor and the horn vibrator 40 are added in parallel to the series connection of the power reception coil 72 and the first capacitor. Even in a system in which the N-P system and the N-S system are combined, equivalent (or higher) performance is expected as compared with a single system.

In the above-described embodiment, the mesh-type nebulizer has been described, but the present invention is not limited thereto. The nebulizer of the present invention can also be applied to an ultrasonic nebulizer having a so-called two-tank structure (that is, a nebulizer of a type in which a chemical tank is immersed in a cooling water tank facing an ultrasonic vibrator, an ultrasonic vibration energy generated from the ultrasonic vibrator concentrates on a surface of a chemical liquid through cooling water, and the chemical liquid is atomized by an action of vibration (a cavitation effect)).

As described above, a nebulizer of the present disclosure is a nebulizer that atomizes and ejects a liquid, the nebulizer comprising:

a main body lower portion; and
a main body upper portion combined with the main body lower portion,
the main body lower portion being mounted with a power supply unit, an oscillation unit that receives a power supply from the power supply unit and generates an oscillation output, and a power transmission-side circuit for transmitting the oscillation output to the main body upper portion,
the main body upper portion being mounted with a power reception-side circuit for receiving the oscillation output, and an atomization portion including an ultrasonic vibrator configured to atomize a supplied liquid using the oscillation output received, and
the nebulizer including a power supply system that performs wireless power supply from the power transmission-side circuit to the power reception-side circuit,
wherein
the power transmission-side circuit includes a power transmission coil and transmits a power to the power reception-side circuit at a certain oscillation frequency through the power transmission coil,
in the power reception-side circuit, a power reception coil and the ultrasonic vibrator as a load including a capacitive reactance configure a power reception-side resonance circuit to determine a resonance frequency of the power reception-side resonance circuit, and
the nebulizer includes a control unit that controls the oscillation frequency so as to maintain a power transmission efficiency from the power transmission-side circuit to the power reception-side circuit when a resonance frequency of the power reception-side resonance circuit changes due to a change in an impedance including the capacitive reactance of the ultrasonic vibrator during power supply.

In the present specification, the "load including a capacitive reactance" refers to an ultrasonic vibrator. The ultrasonic vibrator has piezoelectric ceramics and a pair of electrodes provided with the piezoelectric ceramics interposed therebetween, and the piezoelectric ceramics ultrasonically vibrates when a high-frequency voltage is applied between the pair of electrodes.

In the nebulizer of the present disclosure, when the resonance frequency of the power reception-side resonance circuit changes as the impedance including the capacitive reactance of the ultrasonic vibrator as the load changes during the power supply, the control unit controls the oscillation frequency so as to maintain the power transmission efficiency from the power transmission-side circuit to the power reception-side circuit. Therefore, according to this nebulizer, even when the impedance of the load changes, it is possible to prevent a decrease in the power transmission efficiency from the power transmission-side circuit to the power reception-side circuit. As a result, the atomization portion including the ultrasonic vibrator can stably atomize and eject the supplied liquid using the oscillation output received.

In the nebulizer according to one embodiment,
the control unit
includes a detection unit that detects a voltage value and/or a current value for power transmission in the power transmission-side circuit,
matches the oscillation frequency in the power transmission-side circuit with the resonance frequency of the power reception-side resonance circuit at a start of the power supply,
detects, by the detection unit, a change in an impedance of the power reception-side circuit in accordance with the voltage value and/or the current value in the power transmission-side circuit when the impedance of the power reception-side circuit changes due to the change of the load during the power supply, and
controls the oscillation frequency so as to maintain the power transmission efficiency on a basis of a detection result by the detection unit.

The "voltage value and/or current value" may be one or both of the voltage value and the current value. For example, it may be a voltage-to-current ratio. Each of the voltage value and the current value may be an effective value.

In the nebulizer of this one embodiment, the control unit matches the oscillation frequency in the power transmission-side circuit with the resonance frequency of the power reception-side resonance circuit at a start of the power supply. Note that at the start of the power supply, since the impedance (in particular, the capacitive reactance) of the load has a predetermined value, the oscillation frequency in the power transmission-side circuit can be matched with the resonance frequency of the power reception-side resonance circuit. Furthermore, when the impedance of the power reception-side circuit changes due to the change of the load during the power supply, the control unit detects, by the detection unit, the change in the impedance of the power reception-side circuit in accordance with the voltage value and/or the current value in the power transmission-side circuit. Then, the control unit controls the oscillation frequency so as to maintain the power transmission efficiency on the basis of a detection result by the detection unit. Therefore, it is possible to prevent a decrease in the power transmission efficiency from the power transmission-side circuit to the power reception-side circuit.

In the nebulizer according to one embodiment, in the power transmission-side circuit, the power transmission coil and a capacitor configure a power transmission-side resonance circuit, and a resonance frequency of the power transmission-side resonance circuit is the oscillation frequency, and the control unit controls the resonance frequency of the power transmission-side resonance circuit so as to maintain a tuned state between the power transmission-side resonance circuit and the power reception-side resonance circuit when the resonance frequency of the power reception-side resonance circuit changes due to the change in the load during the power supply.

In the nebulizer of this one embodiment, when the resonance frequency of the power reception-side resonance circuit changes due to the change of the load during the power supply, the control unit controls the resonance frequency of the power transmission-side resonance circuit so as to maintain the tuned state between the power transmission-side resonance circuit and the power reception-side resonance circuit. Therefore, according to this nebulizer, even when the impedance of the load changes, it is possible to prevent a decrease in the power transmission efficiency from the power transmission-side circuit to the power reception-side circuit.

In the nebulizer according to one embodiment, the control unit includes a detection unit that detects a voltage value and/or a current value for power transmission in the power transmission-side circuit, matches the resonance frequency in the power transmission-side resonance circuit with an initial value of the resonance frequency of the power reception-side resonance circuit at a start of the power supply to put the power transmission-side resonance circuit and the power reception-side resonance circuit into the tuned state, detects, by the detection unit, in accordance with the voltage value and/or the current value in the power transmission-side circuit, that an impedance of the power reception-side circuit changes due to the change of the load during the power supply and thus the resonant frequency of the power reception-side resonance circuit shifts from the initial value to an other value, and controls the resonance frequency of the power transmission-side circuit on a basis of a detection result of the detection unit so that the resonance frequency matches the other value to maintain the tuned state between the power transmission-side resonance circuit and the power reception-side resonance circuit.

In the nebulizer of this one embodiment, the control unit matches the resonance frequency of the power transmission-side resonance circuit with the initial value of the resonance frequency of the power reception-side resonance circuit at a start of the power supply, and puts the power transmission-side resonance circuit and the power reception-side resonance circuit into the tuned state. Note that at the start of the power supply, since the impedance (in particular, the capacitive reactance) of the load has a predetermined value, the oscillation frequency in the power transmission-side circuit can be matched with the initial value of the resonance frequency of the power reception-side resonance circuit. Furthermore, the control unit detects, by the detection unit, in accordance with the voltage value and/or the current value in the power transmission-side circuit, that the impedance of the power reception-side circuit changes due to the change of the load during the power supply, and thus the resonance frequency of the power reception-side resonance circuit from the initial value to the other value. Then, the control unit maintains the tuned state between the power transmission-side resonance circuit and the power reception-side resonance circuit by controlling the resonance frequency of the power transmission-side circuit so that the resonance frequency matches the other value on the basis of the detection result by the detection unit. Therefore, it is possible to prevent a decrease in the power transmission efficiency from the power transmission-side circuit to the power reception-side circuit.

In the nebulizer according to one embodiment, the control unit calculates a present oscillation power in the power transmission-side circuit on a basis of the voltage value and the current value detected by the detection unit, and adjusts the oscillation power so that the oscillation power becomes a predetermined target power value when the impedance of the power reception-side circuit changes due to the change of the load during the power supply and thus the oscillation power deviates from the target power value.

In the nebulizer of this one embodiment, the control unit calculates the oscillation power in the power transmission-side circuit on the basis of the voltage value and the current value detected by the detection unit. Further, the control unit adjusts the oscillation power so that the oscillation power becomes the target power value when the impedance of the power reception-side circuit changes due to the change of the load during the power supply and thus the oscillation power deviates from the predetermined target power value. Therefore, the oscillation power in the power transmission-side circuit is maintained at the target power value.

In the nebulizer according to one embodiment, the control unit determines whether or not an error has occurred in which the voltage value in the power transmission-side circuit exceeds a predetermined specified value, the current value in the power transmission-side circuit falls below a predetermined specified value, and/or an oscillation power that is a product of the voltage value and the current value deviates from a predetermined allowable range, and outputs and notifies an alarm signal indicating an occurrence of the error when the error continues for a predetermined time.

The "predetermined time" is, for example, a period (30 milliseconds) corresponding to three control cycles when one control cycle of the control unit is 10 milliseconds.

The "output" of the alarm signal indicates, for example, display (lighting or blinking) of a lamp, generation of a buzzer sound, and the like.

In the nebulizer of this one embodiment, the control unit determines whether or not an error has occurred in which the voltage value in the power transmission-side circuit exceeds a predetermined specified value, the current value in the power transmission-side circuit falls below a predetermined specified value, and/or an oscillation power that is a product of the voltage value and the current value deviates from a predetermined allowable range. Then, the control unit outputs and notifies an alarm signal indicating the occurrence of the error when the error continues for a predetermined time. A user thereof can know the occurrence of the error by the alarm signal. Therefore, for example, the user can take measures such as stopping and restarting the power supply system, and when errors frequently occur, the user can request a service department of a manufacturer to repair the power supply system.

In the nebulizer according to one embodiment, the control unit is mounted in the main body lower portion.

In the nebulizer of this one embodiment, the control unit is mounted in the main body lower portion in addition to the power supply unit, the oscillation unit, and the power transmission-side circuit mounted in the main body lower portion. Therefore, in addition to the power supply unit, the oscillation unit, and the power transmission-side circuit, the control unit is protected by the casing forming the main body lower portion. For example, it is possible to prevent erosion by the liquid.

As is clear from the foregoing, according to the nebulizer comprising the power supply system of this disclosure, even when the impedance of the ultrasonic vibrator as the load changes, it is possible to prevent a decrease in the power transmission efficiency from the power transmission-side circuit to the power reception-side circuit.

The above embodiments are illustrative, and are modifiable in a variety of ways without departing from the scope of this invention. It is to be noted that the various embodiments described above can be appreciated individually within each embodiment, but the embodiments can be combined together. It is also to be noted that the various features in different embodiments can be appreciated individually by its own, but the features in different embodiments can be combined.

The invention claimed is:

1. A nebulizer that atomizes and ejects a liquid, the nebulizer comprising:
   a main body lower portion; and
   a main body upper portion combined with the main body lower portion,
   the main body lower portion being mounted with a power supply unit, an oscillation unit that receives a power supply from the power supply unit and generates an oscillation output, and a power transmission-side circuit for transmitting the oscillation output to the main body upper portion,
   the main body upper portion being mounted with a power reception-side circuit for receiving the oscillation output, and an atomization portion including an ultrasonic vibrator configured to atomize a supplied liquid using the oscillation output received, and
   the nebulizer including a power supply system that performs wireless power supply from the power transmission-side circuit to the power reception-side circuit, wherein
   the power transmission-side circuit includes a power transmission coil and transmits a power to the power reception-side circuit at a certain oscillation frequency through the power transmission coil, in the power reception-side circuit, a power reception coil and the ultrasonic vibrator as a load including a capacitive reactance configure a power reception-side resonance circuit to determine a resonance frequency of the power reception-side resonance circuit, and
   the nebulizer includes a control unit that controls the oscillation frequency so as to maintain a power transmission efficiency from the power transmission-side circuit to the power reception-side circuit when a resonance frequency of the power reception-side resonance circuit changes due to a change in an impedance including the capacitive reactance of the ultrasonic vibrator during power supply.

2. The nebulizer according to claim 1, wherein the control unit
   includes a detection unit that detects a voltage value and/or a current value for power transmission in the power transmission-side circuit,
   matches the oscillation frequency in the power transmission-side circuit with the resonance frequency of the power reception-side resonance circuit at a start of the power supply,
   detects, by the detection unit, a change in an impedance of the power reception-side circuit in accordance with the voltage value and/or the current value in the power transmission-side circuit when the impedance of the power reception-side circuit changes due to the change of the load during the power supply, and
   controls the oscillation frequency so as to maintain the power transmission efficiency on a basis of a detection result by the detection unit.

3. The nebulizer according to claim 1, wherein
   in the power transmission-side circuit, the power transmission coil and a capacitor configure a power transmission-side resonance circuit, and a resonance frequency of the power transmission-side resonance circuit is the oscillation frequency, and
   the control unit controls the resonance frequency of the power transmission-side resonance circuit so as to maintain a tuned state between the power transmission-side resonance circuit and the power reception-side resonance circuit when the resonance frequency of the power reception-side resonance circuit changes due to the change in the load during the power supply.

4. The nebulizer according to claim 3, wherein the control unit
   includes a detection unit that detects a voltage value and/or a current value for power transmission in the power transmission-side circuit,
   matches the resonance frequency in the power transmission-side resonance circuit with an initial value of the resonance frequency of the power reception-side resonance circuit at a start of the power supply to put the power transmission-side resonance circuit and the power reception-side resonance circuit into the tuned state,
   detects, by the detection unit, in accordance with the voltage value and/or the current value in the power transmission-side circuit, that an impedance of the power reception-side circuit changes due to the change of the load during the power supply and thus the resonant frequency of the power reception-side resonance circuit shifts from the initial value to an other value, and
   controls the resonance frequency of the power transmission-side circuit on a basis of a detection result of the detection unit so that the resonance frequency matches the other value to maintain the tuned state between the power transmission-side resonance circuit and the power reception-side resonance circuit.

5. The nebulizer according to claim 2, wherein the control unit calculates a present oscillation power in the power transmission-side circuit on a basis of the voltage value and the current value detected by the detection unit, and adjusts the oscillation power so that the oscillation power becomes a predetermined target power value when the impedance of the power reception-side circuit changes due to the change of the load during the power supply and thus the oscillation power deviates from the target power value.

6. The nebulizer according to claim 2, wherein the control unit determines whether or not an error has occurred in which the voltage value in the power transmission-side circuit exceeds a predetermined specified value, the current value in the power transmission-side circuit falls below a predetermined specified value, and/or an oscillation power that is a product of the voltage value and the current value deviates from a predetermined allowable range, and outputs and notifies an alarm signal indicating an occurrence of the error when the error continues for a predetermined time.

7. The nebulizer according to claim 1, wherein the control unit is mounted in the main body lower portion.

\* \* \* \* \*